US007110818B2

United States Patent
Anderson et al.

(10) Patent No.: US 7,110,818 B2
(45) Date of Patent: Sep. 19, 2006

(54) METHOD AND SYSTEM FOR PROGRAMMING AN IMPLANTABLE CARDIAC DEVICE

(75) Inventors: Thomas N. Anderson, Issaquah, WA (US); Vickie L. Conley, Woodbury, MN (US); David A. Miller, Woodinville, WA (US); Mark Schwartz, Hugo, MN (US); C. Denise Thompson, Eugene, OR (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 683 days.

(21) Appl. No.: 10/012,886

(22) Filed: Nov. 4, 2001

(65) Prior Publication Data
US 2003/0088292 A1   May 8, 2003

(51) Int. Cl.
*A61N 1/37* (2006.01)
(52) U.S. Cl. ....................................... 607/30
(58) Field of Classification Search ............ 607/1–32, 607/60, 59
See application file for complete search history.

(56) References Cited

U.S. PATENT DOCUMENTS

| | | | |
|---|---|---|---|
| 4,208,008 A | 6/1980 | Smith | 371/15 |
| 4,432,360 A | 2/1984 | Mumford et al. | |
| 4,520,825 A | 6/1985 | Thompson et al. | 128/422 |
| 4,809,697 A | 3/1989 | Causey, III et al. | |
| 5,370,672 A | 12/1994 | Fowler et al. | 607/58 |
| 5,603,726 A | 2/1997 | Schulman et al. | 607/57 |
| 5,607,460 A | 3/1997 | Kroll et al. | 607/30 |
| 5,716,382 A | 2/1998 | Snell | 607/30 |
| 5,833,623 A | 11/1998 | Mann et al. | 600/523 |
| 5,891,178 A | 4/1999 | Mann et al. | 607/27 |
| 6,014,581 A | 1/2000 | Whayne et al. | 600/523 |
| 6,052,626 A | 4/2000 | Inui | 700/121 |
| 6,088,618 A | 7/2000 | Kerver | 607/30 |
| 6,249,705 B1 * | 6/2001 | Snell | |
| 6,289,248 B1 | 9/2001 | Conley et al. | 607/59 |
| 6,393,325 B1 | 5/2002 | Mann et al. | 607/46 |
| 6,574,511 B1 * | 6/2003 | Lee | |
| 6,690,972 B1 | 2/2004 | Colney et al. | |
| 6,842,644 B1 | 1/2005 | Anderson et al. | |

FOREIGN PATENT DOCUMENTS

EP   0565084   10/1993

OTHER PUBLICATIONS

Anderson, Thomas N., et al., "User Navigation and Guidance During Configuration and Storage of Parameters for Medical Device", U.S. Appl. No. 11/032,312, filed Jan. 10, 2005, 55 pages.

* cited by examiner

*Primary Examiner*—Scott M. Getzow
(74) *Attorney, Agent, or Firm*—Schwegman, Lundberg, Woessner & Kluth, P.A.

(57) ABSTRACT

Systems and methods for providing a medical device parameter profile to a programmer that is remote from where the parameter profile was created is described. The system includes a first programmer creating a parameter profile for a specific classification. The classes are defined by therapy or patient status. A communication system for communicating the parameter profile to at least one additional programmer that is remote from the first programmer.

28 Claims, 3 Drawing Sheets

METHOD AND SYSTEM FOR PROGRAMMING AN IMPLANTABLE CARDIAC DEVICE

FIELD OF THE INVENTION

The present system and method relates to programming medical devices and, more particularly, to disseminating parameter profiles to medical device programmers.

BACKGROUND

Cardiac rhythm management systems provide therapy to a patient's heart to correct various forms of arrhythmias, such as tachyarrhythmias and bradyarrhythmias. One type of such a system is an implantable cardiac rhythm management ("CRM") device and a programmer for programming the CRM device. As the understanding of various types of arrhythmias has grown since the inception of CRM devices, so has the need to provide a greater variety of therapies with the CRM device. This greater variety of therapies allows a physician to closely tailor the therapy provided by the CRM device to the specific needs of the patient by programming various parameters of the CRM device. The CRM device provides therapy based on the parameters. However, the number of programmable parameters in CRM devices has grown along with the number and complexity of therapies that an individual CRM device can provide. Additionally, not all parameters that can be programmed are necessary or even appropriate for certain therapies. Accordingly, the patient's treating physician uses the programmer to program numerous parameters of the CRM device to achieve the desired therapy. There is a learning curve for learning the system, e.g., hardware and software, to program the parameter profiles that are appropriate for a given therapy. The numerous parameters further increase the time it takes to learn how to program the parameters in the profiles. Consequently, there is a need in the field of CRM systems to simplify the use of parameter profiles.

SUMMARY OF THE INVENTION

The present system includes a first programmer used to create at least one parameter profile. The at least one parameter profile is communicated to a second programmer, which is used to program a medical device. In an embodiment, the medical device is an implantable cardiac rhythm management device. In an embodiment, the medical device is an ICD. In an embodiment, a machine readable media stores the at least one parameter profile. The second programmer reads the parameter profile from the machine readable media. In an embodiment, the at least one parameter profile is communicated over a computer network, telephone lines, or other electrical connection. In an embodiment, the at least one parameter profile relates to a therapy type. In an embodiment, the at least one parameter profile relates to a diagnosis, i.e., the patient's condition.

A method includes creating a parameter profile for a specific therapy or patient condition, communicating the parameter profile to at least one programmer that is remote from the programmer used to create the parameter profile, and transmitting the parameter profile into a medical device using the at least one remote programmer.

Other aspects of the present system and method will be apparent on reading the following detailed description and viewing the drawings that form a part thereof.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

The present method and apparatus will be described in embodiments involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, pacer/defibrillators, biventricular or other multi-site coordination devices, monitors, programmers and recorders.

Figure 1:
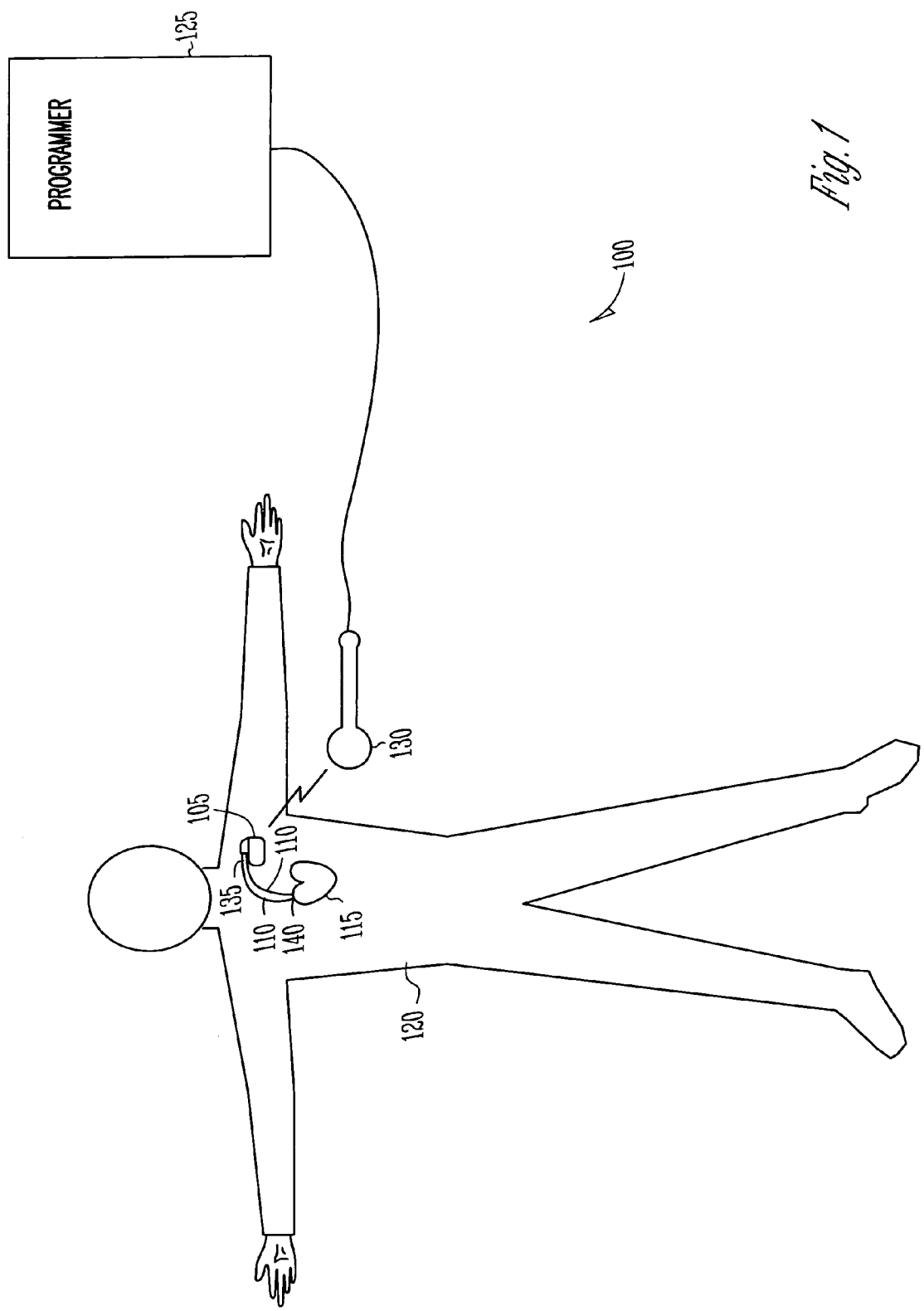
FIG. 1 is a view illustrating generally one embodiment of portions of a cardiac rhythm management system and an environment in which it is used.

FIG. 1 is a schematic illustration of one embodiment a cardiac rhythm management system 100 and an environment in which it is used. System 100 includes an implantable cardiac rhythm management ("CRM") device 105 coupled by intravascular endocardial leads 110, or other lead, to a heart 115 of patient 120. Catheter lead 110 includes a proximal end 135, which is coupled to device 105, and a distal end 140, which is coupled to one or more portions of heart 115. CRM device 105 contains electronic circuitry adapted to perform various tasks associated with cardiac rhythm management. Such tasks include pacing, defibrillating, sensing, storing data, and transmitting data. CRM device 105 includes processing circuits and memory for storing instructions for at least one therapy, a profile of programmable parameters associated with the at least one therapy, and measured patient cardiac data. The processing circuits perform cardiac rhythm management therapy based on the programmed parameters and, in some cases, measured patient cardiac data. Examples of CRM devices include the VENTAK®, PULSAR™, DISCOVERY™, MERIDAN™ and VIGOR™ families of implantable cardioverter defibrillators, automatic implantable cardioverter defibrillators, pacing systems and pacemakers, all by Cardiac Pacemaker, Inc. of St. Paul, Minn. System 100 also includes an external medical device programmer 125 providing wireless communication with device 105 using a communication device 130.

Figure 2:
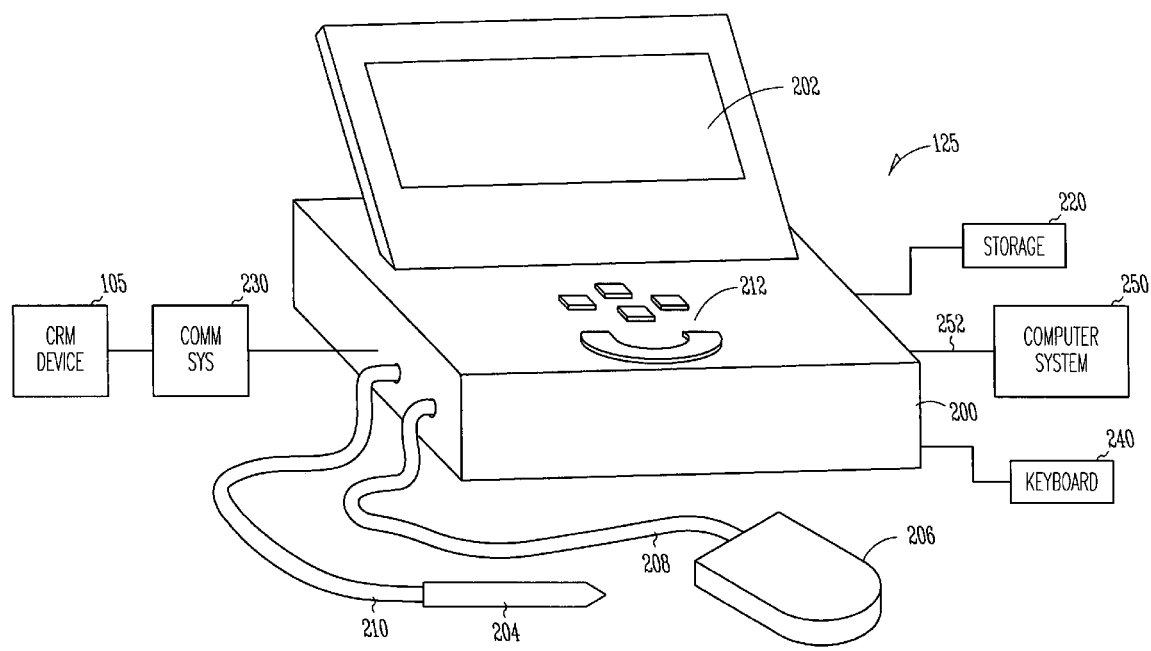
FIG. 2 is a view illustrating a programming system according to an embodiment of the present system.

FIG. 2 shows one embodiment of a medical device programmer 125 of the medical device system. An example of a medical device programmer is the ZOOM™ programming system by Cardiac Pacemaker, Inc. of St. Paul, Minn.

As previously mentioned, one embodiment of the medical device programmer 125 for the implantable CRM device 105 takes the form of an external controller. However, in an alternative embodiment, the medical device system is a completely external device such as an external cardioverting/defibrillator system as are known in the art, where the programmer unit is physically and electronically integrated into electronic control circuitry. In an embodiment, the electronic control circuitry of the external cardioverting/defibrillator system performs the same functions as the implantable CRM device 105 described herein. In an embodiment, the electronic control circuitry of the external cardioverting/defibrillator system is the same as the electronic control circuitry of CRM device 105. An example of this latter embodiment is for an external cardiac monitor and defibrillation unit, electrically connected to the heart by any combination of intracardiac catheters, epicardial electrodes and/or external cardiac electrodes.

Medical device programmer 125 is designed to be positioned external of the human body 120 for communicating with an implantable medical device, such as CRM device 105 in FIG. 1. Such communication includes wireless communication, RF telemetry or signal induction. Medical device programmer 125 has programmer electronic circuitry, including a microprocessor and related circuitry, such as digital memory, which is coupled to an output unit, which is here shown as display screen 202.

In one embodiment, the medical device programmer 125 has an outer housing 200 which is made of metal alloy, a thermal plastic or other suitable lightweight durable material. The display screen 202 is disposed on the upper surface of housing 200. The display screen 202 folds down into a closed position when medical device programmer 125 is not in use, thereby reducing the size of medical device programmer 125 and protecting the display surface of display screen 202 during transportation and storage. In another embodiment, the display screen 202 is fixed in a single position, for example fixed directly on the housing. An embodiment of the present system includes providing the programmer 125 with a video output connection to which a non-integral monitor can be connected. A user interface and/or data may then be displayed on the non-integral monitors. In some embodiments, the external programmer additionally has a non-volatile storage 220, such as machine readable media, floppy disks, internal memory (e.g. BIOS, ROM) and a hard drive, and volatile storage, such as internal memory (e.g. RAM) disposed within the housing.

The medical device programmer 125 is shown with the display screen 202 positioned in one of a plurality of possible open positions such that a display on the display screen 202 is visible to a user situated in front of medical device programmer 125. In one embodiment, the display screen 202 is of a CRT, LCD or electroluminescent type. The display screen 202 is operatively coupled to the electronic circuitry disposed with the housing 200 and is adapted to provide a visual display of graphics and/or data under control of the programmer electronic circuitry, e.g. processor and memory. The processor may be a commercially available processor available from Intel®, Cyrix®, AMD™ or other manufacturers, or may be a dedicated processing circuit specifically designed for a medical device programmer. The processor runs either a commercially available operating systems or specially designed operating systems dedicated to medical device programmers. The memory in the programmer stores software for programming parameters into a profile of parameters for a therapy. The memory further stores programmable parameters that are used by the software to control operation of the CRM device.

Medical device programmer 125 further includes a user input device coupled to the electronic circuitry. In one embodiment, the user input device is the screen 202, which is provided with touch-sensitive capability, such that a user can interact with the programmer electronic circuitry by touching the display area on screen 202 with a finger (not shown), a stylus 204, or other pointing device. In one embodiment, the touch-sensitive display screen is the primary input for the medical device programmer 125. The medical device programmer 125 further includes a programming head 206, which is place over a patient's body near the implant site of an implanted medical device, such as CRM device 105, in order to establish a communication link between CRM device 105 and programmer 125. The communication link between CRM device 105 and programmer 125 allows the electronic circuitry of programmer 125 to be coupled to the electronic control circuitry of the CRM device 105. The programmer 125 sends parameter profiles to the CRM device via the head 206. The programming head 206 is coupled to the electronic circuitry of medical device programmer 125 by a cable 208 and includes a receiver circuit for receiving signals from a transmitter circuit of CRM device 105. Consequently, the programmer 125 remotely monitors and receives data from the CRM device 105. In another embodiment, a communication system 230 is intermediate programmer 125 and the CRM device 105. In an embodiment, the communication system is a telephone system. In an embodiment, the communication system is a computer network such as a LAN, WAN, or global computer network (e.g. internet). In an embodiment, the communication system is an electrical connection via hard wire or wireless connection. In one embodiment, communication system 230 establishes a type of client/server relationship between the CRM device 105 and the programmer 125.

In one embodiment of the system, stylus 204 used to interact with the touch-sensitive display screen 202 is coupled to the programmer electronic circuitry within the housing 200 by a cable 210. In another embodiment of the system, only a touch sensitive screen 202 is provided which is activated by a user's finger touching the screen. Alternatively, medical device programmer 125 may be equipped with a conventional computer "mouse"-type pointing device, rather than a stylus or a touch sensitive screen which is actuatable by a user's finger. In the absence of either a stylus, touch-sensitive screen or a mouse, on-screen cursor control for enabling user interaction with medical device programmer 125 may be facilitated through cursor control keys 212 (arrow keys or the like) disposed on medical device programmer 125. Another embodiment in lieu of the touch sensitive screen, mouse, or stylus, is providing a serial connection on the programmer 125 for using a keyboard 240 as the input device.

Programmer 200 is also connectable to a computer system 250, for example direct connection through parallel ports or universal bus, modems over telephone connections, LAN, WAN, or other global computer network connections, all represented at 252 in FIG. 2. The present system allows computer system 250 to store CRM device parameter profiles. These profiles are downloaded to the programmer 200, for example over connection 252 or by downloading the profile to a portable data storage medium and loading the profile from the medium to the programmer 125 for subsequent programming of CRM device 105.

In an embodiment, the computer system 250 is another programmer which is used to create a parameter profile. In an embodiment of the present invention, the preparation of the parameter profile is performed using the techniques described in a U.S. patent application, filed on Nov. 2, 2001, titled "USER NAVIGATION AND GUIDANCE DURING CONFIGURATION AND STORAGE OF PARAMETERS FOR MEDICAL DEVICE", hereby incorporated herein by reference for any purpose.

Figure 3:
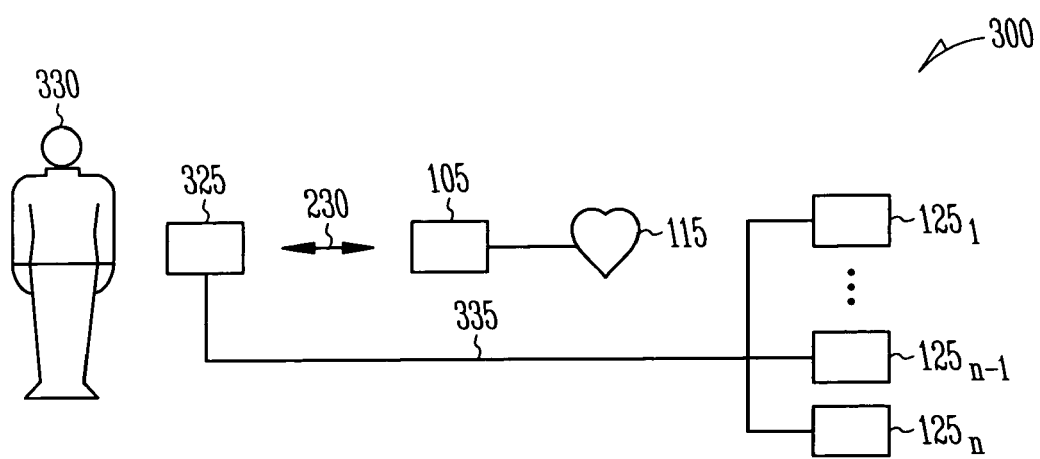
FIG. 3 is a view illustrating a programming system according to an embodiment of the present system.

FIG. 3 shows a system 300 according to an embodiment of the present invention. System 300 includes at least one field programmer 125. In the illustrated embodiment, system 300 includes a plurality of field programmers $125_1, \ldots, 125_n$ and $125_{n-1}$. The field programmers 125 are used to transmit a parameter profile to a medical implant such as a CRM device. System 300 also includes a further, master programmer 325 that is remote from field programmers 125. In an embodiment, master programmer 325 is the same as the field programmer 125 as described herein. Master programmer 325 communicates with a CRM device 105 through a communication system 230. A user 330 creates a parameter profile, which is stored in master programmer 325. The master programmer 325 provides the parameter profile to at least one of the plurality of field programmers 125 through a distribution system 335. In an embodiment, the distribution system 335 is machine readable media. In an embodiment, the machine readable media is magnetic media such as floppy disks, tape, etc. In an embodiment, the machine readable media is optical media such as CDs, DVDs, etc. In an embodiment, the distribution system 335 is a telephone system with the master programmer 325 having a communication device connected to the telephone system. The receiving field programmer 125 also includes a communication device. An example of the communication device is a modem.

In another embodiment, the distribution system 335 is a computer network over which the master programmer 325 can send the parameter profile to at least programmer 125. In an embodiment, the distribution system 335 is itself a data storage unit to which the master programmer 325 uploads the parameter profile. Distribution system 335 stores the parameter profile. In an embodiment, the distribution system stores a plurality of parameter profiles. The field programmers 125 download the parameter profile from the distribution system 335. The distribution system 335, in an embodiment, is an indexed database that stores the parameter profiles in a searchable format for the field programmers 125 to find and download. The data storage unit includes a global computer network website, file transfer protocol (ftp) location, bulletin board, or other computer remote access unit.

The present invention allows a user to create parameter profiles at a single location, e.g., at master programmer 325. The user can be a clinical and/or CRM device expert, which would provide remote medical personnel with parameter profiles as initial parameter profiles for a specific therapy or class of patients. Thus, medical personnel that are not as familiar with the parameter profile for a given CRM device or a given diagnosis or therapy the ability to use parameter profiles that were created by users with expertise with the particular classification of therapy or device. As an example, a user of a field programmer who is well versed in tachy therapies and settings may diagnose a patient in need of brady therapy. This user can acquire an initial parameter profile for brady therapy from a clinical expert via the system according to the present invention. It will be understood that the present invention is not limited to this example but includes other types of initial parameter profiles.

The present invention provides medical personnel with a plurality of initial parameter profiles, each of which is specific to a particular class. The class, in an embodiment, is defined by a patient's condition or diagnosis. Examples of such classes include, but are not limited to, (1) an active patient in need of only tachy therapy, (2) an active patient in need of tachy and brady therapy, (3) a sedentary patient in need of tachy and brady therapy, (4) a sedentary patient in need of tachy and brady therapy with a heart block, and (5) a patient prone to atrial fibrillation in need of ventricular tachy therapy. The class, in an embodiment, is defined as a particular therapy. Examples of such classes include, but are not limited to (1) two tachy zones with DDDR pacing, (2) three tachy zones with VDDR pacing, (3) two tachy zones with ATP and DDDR pacing, (4) three tachy zones with monitor-only in VT1 zone, and (5) two tachy zones with DDDR pacing with MTR=140.

Programmers and/or CRM devices sometimes include a nominal parameter profile that must be modified to match the needs of a patient before the CRM device provides the therapy. The present invention provides a system and method for providing a parameter profile that causes the CRM device to provide a specific therapy. In an embodiment, this parameter profile differs from the nominal parameter profile set in the programmer or CRM device In an embodiment, the distribution system 335 is a bidirectional communication system. In addition to sending initial parameter profiles to the field programmers 125, the field programmers 125 can send data back to the master programmer 325. The data send from the field programmer 125 includes parameters changed during use of the initial parameter profile in the field programmer 125. Thus, the master programmer 325 can track how many and what changes are made to an initial parameter profile outside of the master programmer 325.

The system of the present invention allows users with experience in providing therapy with a CRM device to create initial parameter profiles before such profiles are needed in the field. The profiles are stored in memory. The profiles are sent out to clinicians in the field. The field clinicians use the profiles as a basis to begin programming a CRM device to provide appropriate therapy to a patient. Thus, the field clinicians do not begin creating a parameter profile from the same default settings stored in the programmer. Instead the field clinicians load an initial parameter profile that was previously created to begin creation of a parameter profile. In an embodiment, the initial parameter profile was created remotely from the field programmer used by the field clinician. The initial parameter profile is electrically or electromagnetically transmitted from the remote programmer or storage location to the field programmer.

Although specific embodiments have been illustrated and described herein, it will be appreciated by those of ordinary skill in the art that any arrangement which is calculated to achieve the same purpose may be substituted for the specific embodiments shown and described. This application is intended to cover any adaptations or variations of the present system, including and not limited to changes in hardware and software, without departing from the scope of the present system. Moreover, one of ordinary skill in the art will appreciate that the invention can be implemented in a procedural design environment or any other design environment that provides the required relationships. One of skill in the art, upon reading the present disclosure, will further appreciate that the names of the methods and apparatus are not intended to limit embodiments of the system. Furthermore, additional methods and apparatus can be added to the components, functions can be rearranged among the components, and new components to correspond to future enhancements and physical devices used in embodiments of the system can be introduced without departing from the scope of the present invention. One of skill in the art will readily recognize that embodiments of the system are applicable to future medical device programmers.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

The invention claimed is:

1. A cardiac rhythm management device programming system, comprising:
   a first programmer including a user interface used to input a first parameter set for a medical device, the first parameter set being customized for a first class of patient to be treated by the medical device;
   a memory for storing the first parameter set; and
   a second programmer capable of receiving the first parameter set from the memory, the second programmer including a transmitter capable of sending the first parameter set to the medical device.

2. The system of claim 1, wherein the user interface includes a parameter input sequence.

3. The system of claim 1, wherein the memory is a data storage media, and the second programmer includes a data storage media reader.

4. The system of claim 3, wherein the data storage media is a magnetic media, and wherein the data storage media reader is a magnetic media reader.

5. The system of claim 3, wherein the data storage media is an optical media, and wherein the data storage media reader is an optical reader.

6. The system of claim 1, wherein the first programmer includes a transmitter for transmitting the first parameter set to the second programmer, and the second programmer includes a receiver for receiving the first programmer set and a memory for storing the first programmer set.

7. The system of claim 6, wherein the transmitter of the first programmer wirelessly transmits the first parameter set to the receiver of the second programmer.

8. The system of claim 6, wherein the transmitter of the first programmer transmits the first parameter set over an electrical connection to the receiver of the second programmer.

9. The system of claim 8, wherein the electrical connection is a computer network.

10. The system of claim 8, wherein the electrical connection is a telephone line.

11. The system of claim 1, wherein the first programmer includes a second parameter set customized for a second class of patient to be treated by the medical device.

12. The system of claim 11, wherein the second programmer stores the first parameter set and the second parameter set.

13. The system of claim 1, wherein the second programmer includes a memory storing the first parameter set, and wherein the second programmer is capable of programming a plurality of cardiac rhythm management implants with the stored first parameter set.

14. The system of claim 1, further comprising a plurality of the second programmers.

15. A cardiac device programming system, comprising:
   a first programmer including a user interface used to input a parameter set for a cardiac device, the parameter set being customized for a first class of patient to be treated by the cardiac device;
   a bidirectional communication system connected to the first programmer;
   a second programmer capable of receiving the parameter set through the communication system, the second programmer including a transceiver capable of sending the parameter set to the cardiac device and receiving data from the cardiac device; and
   wherein the second programmer is capable of sending the data to first programmer.

16. The system of claim 15, wherein the first programmer includes a user interface, wherein the user interface is adapted to adjust the parameter set based on the data and create an adjusted parameter set, the second programmer receiving the adjusted parameter set and sending the adjusted parameter set to the cardiac device.

17. The system of claim 15, wherein the first programmer includes an analyzer that adjusts the parameter set based on the data received from the second programmer.

18. The system of claim 17, wherein the analyzer includes a user interface that receives parameter adjustments from a user to create the adjusted parameter set.

19. The system of claim 18, wherein the adjusted parameter set is individualized for a specific patient under going therapy by the cardiac device.

20. The system of claim 19, wherein the data is cardiac data.

21. The system of claim 15, further comprising a plurality of second programmers.

22. A method, comprising:
   creating a parameter profile for a programmable medical implant using a first programmer;
   storing the parameter profile;
   transmitting the parameter profile to a second programmer;
   programming a medical implant based on the parameter profile using the second programmer.

23. The method of claim 22, wherein programming the medical implant includes sending an unaltered parameter profile to the medical implant.

24. The method of claim 22, wherein programming the medical implant includes modifying the parameter profile and then sending the modified parameter profile to the medical implant.

25. The method of claim 22, wherein transmitting the parameter profile includes transmitting the parameter profile to a plurality of second programmers.

26. The method of claim 22, wherein creating the parameter profile includes creating the parameter profile for a classification to be treated by the medical implant.

27. The method of claim 26, wherein the classification is defined by patient type.

28. The method of claim 26, wherein the classification is defined by therapy type.

* * * * *